(12) United States Patent
Gouma

(10) Patent No.: US 12,016,671 B2
(45) Date of Patent: Jun. 25, 2024

(54) METHOD FOR DETECTING AND MONITORING EXHALED BREATH

(71) Applicant: Ohio State Innovation Foundation, Columbus, OH (US)

(72) Inventor: Pelagia I. Gouma, Columbus, OH (US)

(73) Assignee: Ohio State Innovation Foundation, Columbus, OH (US)

(*) Notice: Subject to any disclaimer, the term of this patent is extended or adjusted under 35 U.S.C. 154(b) by 817 days.

(21) Appl. No.: 16/932,324

(22) Filed: Jul. 17, 2020

(65) Prior Publication Data
US 2021/0015399 A1    Jan. 21, 2021

Related U.S. Application Data

(60) Provisional application No. 62/875,289, filed on Jul. 17, 2019, provisional application No. 62/875,306, filed on Jul. 17, 2019.

(51) Int. Cl.
*A61B 5/08* (2006.01)
*A61B 5/00* (2006.01)
*G01N 33/497* (2006.01)

(52) U.S. Cl.
CPC .......... *A61B 5/082* (2013.01); *A61B 5/4884* (2013.01); *G01N 33/497* (2013.01); *A61B 2503/22* (2013.01); *G01N 2800/122* (2013.01); *G01N 2800/7038* (2013.01)

(58) Field of Classification Search
None
See application file for complete search history.

(56) References Cited

U.S. PATENT DOCUMENTS

| | | | |
|---|---|---|---|
| 2010/0143503 A1* | 6/2010 | Szabo | A61K 33/04 604/23 |
| 2013/0115706 A1* | 5/2013 | Gouma | G01N 27/125 436/116 |
| 2016/0331272 A1* | 11/2016 | Ahmad | A61B 5/082 |
| 2017/0284999 A1* | 10/2017 | Maric | G01N 33/0037 |
| 2018/0252690 A1* | 9/2018 | Yokoyama | G01N 33/0037 |

OTHER PUBLICATIONS

Kalinchuk; Sleep Deprivation Triggers Inducible Nitric Oxide-Dependent Nitric Oxide Production in Wake-Active Basal Forebrain Neurons The Journal of Neuroscience, Oct. 6, 2010 · 30(40):13254-13264 (Year: 2010).*

* cited by examiner

*Primary Examiner* — Jay B Shah
(74) *Attorney, Agent, or Firm* — Wood Herron & Evans LLP

(57) ABSTRACT

A method for measuring levels of specific biomarkers in exhaled breath. Specific compounds such as nitric oxide and isoprene can be monitored from a subject's breath. The resultant measurements can provide indications of the subject's medical condition, or response to an applied stress.

13 Claims, 1 Drawing Sheet

METHOD FOR DETECTING AND MONITORING EXHALED BREATH

RELATED APPLICATIONS

This application is a non-provisional application claiming priority to U.S. Patent Application Nos. 62/875,289 and 62/875,306 both of which were filed on Jul. 17, 2019, the entireties of which are incorporated herein by reference.

BACKGROUND

The condition of a subject, typically a human but the term can include other mammals or breathing organisms, is often evaluated by the collection of a material sample specific to that subject. For example, aspects of the condition of a human may be ascertained by removing and analyzing a blood sample, or a urine sample, a sample of spinal fluid, or other liquid generated by the subject. The collected sample is in turn analyzed for the presence, absence, or concentration of a variety of chemicals which may be indicative of the existence of an ailment affecting the subject, or alternatively as an indicator of the general health of the subject. This type of information can be quantified by conducting analyses of the sample using a range of equipment such as spectrographic or electrophoretic devices, among others. In addition, equipment capable of generating imaged data of the subject can also be used to evaluate a subject's condition. Non-limiting examples include magnetic resonance imaging, x-ray imaging, and electrocardiography.

Another means for obtaining information on various chemical compositions present in a subject is the analysis of the subject's breath. Breath gas consists of inorganic gases such as nitrogen, oxygen, carbon dioxide, and water vapor as well as trace amounts of volatile organic compounds (VOC). The different types of VOCs vary from several hundreds to thousands (Pauling, Phillips et al. 1999, Miekisch et al. 2004). Of these various VOCs, however, only a few are considered to be produced within the body by physiological biochemical processes, in other words being endogenous. Such endogenous materials include acetone, isoprene, ethanol, and methanol. Biological markers, or biomarkers, are defined by the National Institutes of Health, Director's Initiative on Biomarkers and Surrogate Endpoint as follows: "A characteristic that is objectively measured and evaluated as an indicator of normal biological processes, pathogenic processes, or pharmacologic responses to a therapeutic intervention". Biomarkers find many applications in disease diagnosis and health status monitoring, either as diagnostic tools for disease; as tools to determine the stage of the disease or as a classification of the extent of the disease; as indicators of disease prognosis; and as theragnostics for the prediction and monitoring of the clinical response to an intervention.

Breath analysis involves the identification and quantification of single or multiple compounds in the exhaled breath of a subject and is used to diagnose certain diseases or metabolic functions. The concept dates back to antiquity and the time of Hippocrates of Kos. Physicians from that time to the present have been known to diagnose a particular disease with clues from the aroma in the patient's breath. Thus, a subject with uncontrolled diabetes could have exhaled breath with a fruity odor. A subject with advanced liver disease could have a musty, fishy breath. A subject with failing kidneys could have breath with a urine-like smell, and a subject with a lung abscess could transmit a putrid stench. In 1784, Antoine Laurent Lavoisier, the father of the "chemical revolution", found that animals consume oxygen and expire carbon dioxide. Together with French scientist Pierre Simone Laplace, Lavoisier measured the breath of guinea pigs. Theirs was a pioneering work on breath analysis by a chemical method. In 1971, Linus Pauling first analyzed approximately 250 compounds in human breath by gas chromatography and mass spectroscopy.

Breath analysis has several advantages over biomarker sampling methods which would include liquid sampling of blood, urine, as well as biopsy evaluations, endoscopy, and imaging. Breath analysis is completely noninvasive, and with regard to frequency, access, and cost, it is considered simple for any patient of virtually any age to be able to provide a breath sample. In addition to being noninvasive, breath analysis is nonintrusive and a repeatable way to capture and analyze signaling biomarkers.

A challenge in conducting breath analysis is the need to detect and discriminate among signaling metabolites, such as disease markers, and a complex fluid-like exhaled breath, and measuring those metabolites and trace concentrations down to as low as a few parts per billion levels. There is a need for a specific and high affinity between the sensing element and the biomarker.

SUMMARY OF THE INVENTION

The invention described herein is directed to the monitoring of changes in specific exhaled breath biomarkers of the subject, those biomarkers being nitric oxide (NO) and isoprene. In particular, the monitoring of these two exhaled breath biomarkers demonstrates particular benefits in connection with evaluating the physiological changes of a subject who is functioning at high altitudes and experiencing high G-accelerations, such as with a fighter pilot operating an aircraft. The physiological changes result from a change in the oxygen partial pressure within the subject's environment and within the body itself, which are manifested as hypoxia-related episodes.

Individually, as a biomarker, the monitoring of NO can be useful in evaluating for the presence of the flu, and certain respiratory diseases such as asthma and high altitude pulmonary edema (HAPE), and diseases which trigger an inflammatory response in the subject. Isoprene has been found to increase in concentration when acute hypoxic episodes occur to pilots in high altitude flights. Isoprene is also used to monitor metabolic changes in a subject, such as in connection with hypoglycemia, and can be used in the monitoring of sleep-related diseases such as insomnia and sleep apnea of various types, including obstructive sleep apnea, central sleep apnea, and mixed sleep apnea.

Monitoring and studying the changes in a subject's nitric oxide and isoprene breath biomarkers are considered important in evaluating the biophysical, biochemical, and physiological mechanisms that lead to the physiological episodes manifesting hypoxia in, for example, fighter pilots during aircraft operation as well as in individuals exposed to high altitudes in general, and in an alternate application potentially with critical care patients. The invention to conduct this nature of analysis includes the use of a binary (2-sensor array) breath gas sensing system for the continuous monitoring of nitric oxide and isoprene in exhaled breath. The usefulness of the sensor and associated data processing equipment provides information on lung function and metabolic changes of the subject exposed to high altitudes and high accelerations, such as with a fighter pilot in an active operational condition or mode. The 2-sensor array would also provide subject information on critical care patients and may help to predict when changes in patient condition are likely to take effect. Associated with this function of the system is the ability to adopt best practices and oxygenating affected individuals to prevent the onset of hypoxia-like episodes. This method of monitoring can be performed by a sensor device included in or found as part of a mechanical ventilation device, a positive airway pressure device, an electrical stimulation device, any protective helmet, or an oxygen/respiratory mask.

The method includes use of an array of two sensors, one nitrogen oxide sensor based on γ-$WO_3$ and an isoprene sensor based on h-$WO_3$ in tandem. These individual sensors can be exposed to a single incidence of exhaled breath, but are discrete units with the individual metal oxide materials applied to separate electrodes, which in turn are isolated one from the other on substrate materials, typically alumina. The electrode is prepared from platinum or gold, and may be interdigitated in design. In the instance of evaluating the medical status of a pilot, the sensors will retrofit into the pilot's oxygen mask to continuously monitor the concentrations of these two biomarkers in the exhaled breath of the subject and correlate it with the flow of exhaled air. The breath gas sensing system can generate reproducible results by receipt of a single breath. Response time to an exhaled breath is about 15 seconds during continuous monitoring. In this situation the resistance or conductance of the sensor array will change according to the change in the gas concentration of, for example, the pilot's breath. Distinct measurements can be obtained in about 90 seconds, which allows the sensors to return to baseline. As used herein, the concept of continuously monitoring the concentrations of the biomarkers means that measurements from the subject's exhaled breath can be taken in three minute intervals, or less.

In the case of monitoring a pilot's breath, readings of the two sensors will then automatically adjust the oxygen flow in the pilot's mask. This sensor array can also be utilized to assist a critical care patient, to evaluate these biomarkers and automatically adjust the oxygen flow rate for that patient.

DETAILED DESCRIPTION OF THE INVENTION

Figure 1:
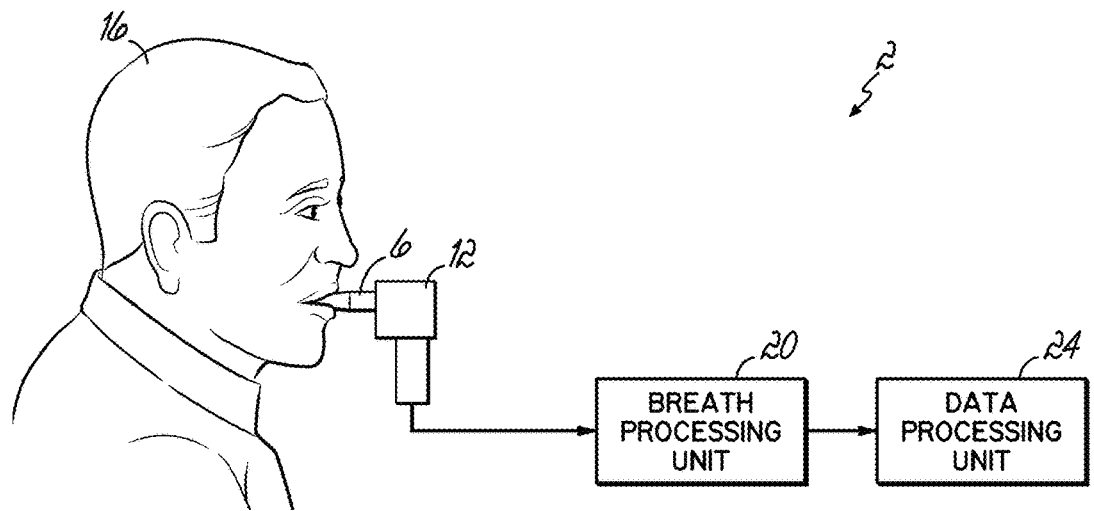
FIG. 1 is a schematic diagram showing of a subject exhaling breath into a receiver coupled to a breath processing unit, that unit in turn coupled to a data processing unit in operation of the invention.
Figure 2:
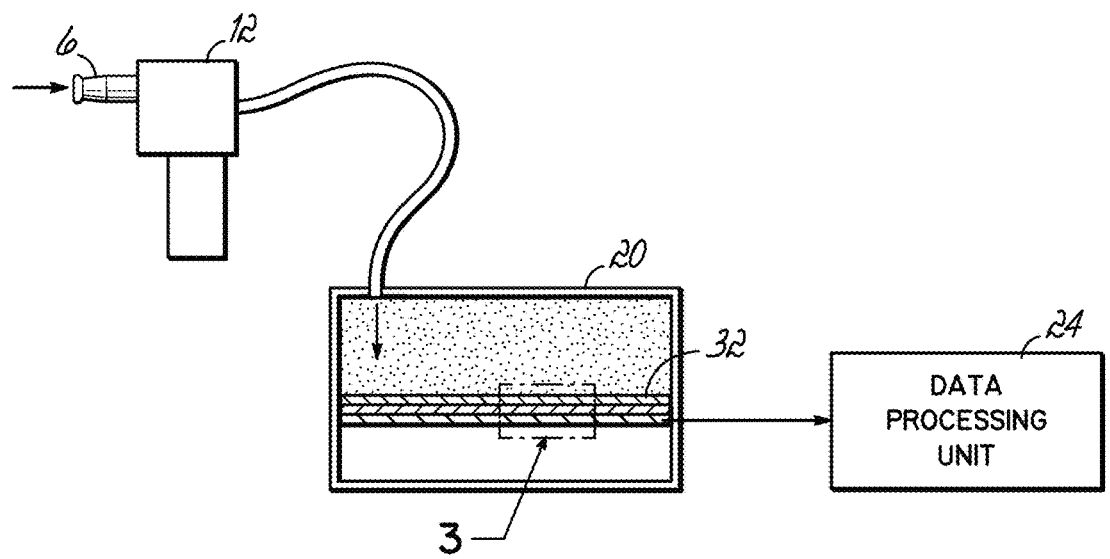
FIG. 2 is a schematic drawing in further detail showing exhaled air particles containing biomarkers of interest in a breath processing unit, that unit in turn coupled to a data processing unit.

The invention in its broader aspects is directed to a method for measuring levels of nitric oxide and isoprene in exhaled breath from a subject comprising exhaling breath into a receiver, transferring the breath into a breath processing unit connected to the receiver and heated within a range of 25° C. to 400° C.; contacting the exhaled breath with a surface of γ-$WO_3$ inside the breath processing unit which responds to nitric oxide, and a surface of h-$WO_3$ inside the breath processing unit which responds to isoprene, to alter an electrical property of the γ-$WO_3$ surface and the h-$WO_3$ surface; and correlating the electrical property of the γ-$WO_3$ surface with a concentration of nitric oxide in the exhaled breath, and the electrical property of the h-$WO_3$ surface with a concentration of isoprene in the exhaled breath. The invention is further directed to a method wherein measurements are taken continuously. The receiver and breath processing unit may be discrete physical components, or may be combined into a single, multiple function unit. A data processing unit receives information on sensor conductance or resistance changes from the breath processing unit. The data processing unit may be a discrete physical component, or may be combined into a single unit with the breath processing unit. As an alternative to monitoring changes in conductance or resistance, the metal oxide may also exhibit a change in optical property associated with a particular biomarker concentration.

The receiver operates typically at an elevated temperature. The exhaled breath gases are to be maintained in the vapor phase, and the selectivity of the metal oxide surface to the particular biomarker is at least partly a function of the particle size of the metal oxide film. In an embodiment, the temperature is in the range of 150 to 400° C. In another embodiment, the temperature is in the range of 200 to 350° C. In another embodiment, the temperature is in the range of 250 to 350° C.

The breath sensor apparatus, to be useful in a dynamic situation such as operation of an aircraft by a fighter pilot, but also in connection with other applications such as monitoring critical care patients in the hospital, must be able to detect biomarkers in the parts per billion concentration range. In addition, the sensor must be able to rapidly receive, prepare, and measure the biomarker components in exhaled breath to be able to allow prompt response to the condition revealed near in time to the receipt of the exhaled breath.

As shown in Table 1 below, from A. Amman and D. Smith, entitled "*Breath Analysis for Clinical Diagnosis and Therapeutic Monitoring*", World Scientific, Singapore 2005, a number of endogenous biomarkers are formed in connection with a variety of activities within the subject, and the physiological ranges can be as low as 1 part per billion (ppb). In fact, studies suggest that measuring biomarkers exhaled in breath show better repeatability in their measured values as opposed to conducting analogous studies utilizing drawn blood samples.

TABLE 1

| Biomarkers | Physiological origin | Related diseases | Physiological ranges in human breath |
| --- | --- | --- | --- |
| Ethane | Lipid peroxidation | Oxidative stress | 1-11 ppb |
| Pentane | Lipid peroxidation | Oxidative stress | Less than ethane |
| Isoprene | Cholesterol biosynthesis | Cholesterol metabolic disorder | 55-121 ppb; 12-580 ppb; |
| Acetone | Decarboxylation of acetoacetate and acetyl-CoA | Diabetes mellitus, ketonemia | 293-870 ppb; 1.2-1880 ppb |
| Ethanol | Alcohol ingestion | Alcohol poisoning | 27-153 ppb; 13-1000 ppb |

TABLE 1-continued

| Biomarkers | Physiological origin | Related diseases | Physiological ranges in human breath |
|---|---|---|---|
| Methanol | Degradation of natural pectin from plants; ingestion | Methanol intoxication | 160-2000 ppb |
| $NH_3$ | Metabolic product of amino acid deamination | Uremia, kidney impairment | 422-2389 ppb; 200-1750 ppb |
| CO | Inhalation from incomplete burning of carbon containing fuels, e.g. smoking | Lung diseases | <6 ppm |
| NO | L-arginine oxidation | Asthma, lung diseases | 1-9 ppb, lower respiratory; 0.2-1 ppm, upper respiratory 1-30 ppm, nasal level |

One of the materials identified in Table 1 is nitric oxide (NO). Nitric oxide is a biomarker affecting major biological processes which include both local and systemic inflammation and carcinogenesis, and has been extensively studied in the context of evaluating the susceptibility of a subject to pulmonary and cardiac diseases, such as high altitude pulmonary edema. Nitric oxide is excreted in human airways and is detectable in exhaled air in significant amounts ranging from 0.221 ppm in the upper respiratory tract and 1 to 30 ppm at the nasal level. Measuring its fractional concentration in exhaled breath (FENO) provides for a quantitative, noninvasive, simple, and safe method of measuring airway inflammation that provides a complementary tool to other ways of assessing airway diseases such as infections and asthma.

Another Table 1 material is isoprene. This compound is endogenously produced in the body at varying levels correlated, for example, to certain metabolic functions of the subject. Isoprene concentration levels in exhaled breath may also be an indicator for sleep disorders and inflammatory conditions.

The $\gamma$-$WO_3$ and h-$WO_3$ sensors described herein are chemo-resistive sensors based on semiconducting metal oxides (SMOs). The sensors herein employ a crystallo-chemical approach to selective chemosensing, wherein the sensor probes target a specific gas or a class of gases. A nano-sensing probe for NO was developed based on the gamma phase polymorph of $WO_3$. The sensitivity of cubic $ReO_3$-type $WO_3$ toward nitric oxide is understood to be dominated by the adsorption-based sensing mechanism that does not affect the bonds on the metal oxide surface. Due to higher oxygen mobility at elevated temperatures or in the presence of reducing atmospheres, oxygen vacancies are formed in metal oxides. The slightly reduced metal oxides may be re-oxidized by either pure oxygen or oxidizing gases such as nitrogen dioxide ($NO_2$). An adsorption-based sensing mechanism involves incorporation of oxygen into these vacancies in the presence of an oxidizing gas such as $NO_2$ or NO.

$WO_3$ has a very complex set of electronic properties where it can range from being a metallic conductor in its highly reduced state to an insulator. Cubic $WO_3$ with the ideal $ReO_3$ lattice is difficult to obtain as a stable polymorph. Polymorphic transformations of the pseudo-cubic lattice result in this wide variation in the electronic properties of $WO_3$. $WO_3$ usually crystallizes in one of the following crystal structure modifications—triclinic, monoclinic, orthorhombic, and tetragonal. All of these polymorphs are distorted forms of a cubic $ReO_3$ lattice, with increasing order of crystallographic symmetry from the triclinic to the tetragonal lattice. The crystal lattice is composed of a framework of metal-oxygen octahedra where the metal atoms are located at their centers with varying amounts of metal-oxygen bond lengths and thus varying amounts of octahedral distortion. This distortion in turn serves to stabilize the different polymorphs.

Another thermodynamically metastable form of $WO_3$ that has been synthesized and reported has a hexagonal structure (h-$WO_3$). The crystal structure is unique in that the lattice is made up of rings of corner sharing oxygen octahedra. The octahedral units are arranged in layers normal to the hexagonal c-axis. The layered oxygen octahedra provides both triangular and hexagonal prism channels that allow for easy movement of ions or gas molecules to travel through the lattice. Tungsten bronzes frequently crystallize in a hexagonal lattice, when the hexagonal tunnels are interpolated with specific cations.

To prepare the nitric oxide sensor, $\gamma$-$WO_3$ nanoparticles were synthesized by a flame spray pyrolysis method using a lab scale nano powders production system from Tethis (NP10). The system contains three main parts: a nozzle unit, a dispensing system, and a control unit, which were all located in a lab-vented fume hood. The system was controlled by a computer, which controls the safety and accuracy of the synthesis process. A collecting system was based on glass fiber filters on top of the collecting chamber. The precursor solution was prepared as follows. 0.3 M of tungsten (VI) isopropoxide (99% All Chemie) was dissolved into propanol in a nitrogen atmosphere glovebox. After aging for a day, the precursor was supplied at a rate of 5 mL/min through the Tethis flame nozzle and dispersed by oxygen with a rate of 5 standard liters per minute (slm) to form a fine spray. The fine spray was ignited and supported by the flame that was the combustion product of methane and oxygen at the rate of 31.5 slm and 3.0 slm respectively. The synthesized particles were deposited beneath a glass fiber filter (Whatman) and collected after the process was completed. The sensor was connected to a TO-8 electrode pin package through gold wires (Alfa Aesar, 0.25 mm diameter, 99.998%) bonded on the integrated platinum circuits on an alumina ($Al_2O_3$) substrate. A heater was mounted below the sensor and adhered to the sensor using alumina paste to improve heat conduction. One operating temperature of the sensor used for conducting experiments was 200° C. The sensor component within the breath processing unit 20 is removable, allowing for replacement of this component at the end of its useful lifetime of about 1000 measurements.

To prepare the h-$WO_3$ sensor, an acid precipitation method was used. This method is described as follows. 1.17 g of sodium tungsten hydrate $Na_2WO_4·2H_2O$ of analytical grade was dissolved in 17 mL of water and the solution was cooled to 10° C. To this, 8.4 mL of normal hydrochloric acid solution (analytical grade 18% in excess of equimolar reaction) cooled to the same temperature was added in one dose.

The mixture was returned to a refrigerator and allowed to age for about 20 hours. The following reaction took place —$Na_2WO_4 \cdot 2H_2O + H^+ = H_2WO_4 \cdot 2H_2O + NH^+$ and the whole mixture turned into a whitish gel. Then, 110 mL of water were added to the vessel, and the gel and water were lightly stirred manually. The supernatant liquid was removed by centrifuging the mixture. Then, 130 mL of water were added to the precipitate, and the three steps of light manual stirring, centrifuging, and removal of supernatant liquid were repeated several times to obtain $H_2WO_4 \cdot H_2O$, the precursor of the final h-$WO_3$ powders. $H_2WO_4 \cdot H_2O$ suspensions were passed to hydrothermal dehydration and carried out in Parr acid digestion bombs at 125° C.±5° C. The material was then dehydrated under air at a furnace temperature of 300-330° C., and an annealing time of 90 minutes. This layer deposition of the h-$WO_3$ was carried out using the nano powder production system from Tethis (NP10). The color of the synthesized h-$WO_3$ was gray. There are typically two shapes of grains: equiaxed particles and rod-shaped particles. These two shapes were mixed together, and with the rods being the majority portion. There was a certain dispersion of the diameter distribution, from 20 to 50 nm, with an average size of 35 nm. The high resolution transmission electron microscope (HRTEM) image and the selected area diffraction pattern (SAED) confirmed that these particles were polycrystalline and could be indexed in the h-$WO_3$ structure. The diameters of the rods were 30-100 nm with an average value of 50 nm, and their lengths were up to 100-300 nm with an average value of 200 nm. The HRTEM image recorded the lattice of the h-$WO_3$ planes with an inter-planar spacing of about 0.39 nm, indicating the $WO_3$ rods were single crystalline in most regions and grew along the [001] direction, which is consistent with the SAED.

To stabilize the h-$WO_3$ sensor, a heat treatment was applied to remove residual tungsten hydrate byproduct. This heat treatment was performed at 350° C. for eight hours. h-$WO_3$ showed a sensitive and selective detection of isoprene at 350° C. The sensitivity of the h-$WO_3$ sensored isoprene is 7.34 which is higher than any other gas.

In operation, sensor apparatus 2 was comprised of a mouthpiece 6 coupled to a receiver 12 for receiving the exhaled breath from the subject 16.

The collected breath was then passed to a breath processing unit 20. Electronic information generated by the breath processing unit 20 then was transferred to the data processing unit 24. The measurement by the two different (NO and isoprene) sensors can be simultaneous.

As shown herein, the receiver 12, breath processing unit 20 and data processing unit 24 are identified as being discrete, separate devices. However, the showing of these individual components as separate elements is provided for ease of description. It is also possible that one or more of these individual components would be coupled together into a single operating device depending on the particular applications and structural limitations for this device depending on the particular applications required for this particular sensor apparatus. Thus, the mouthpiece and receiver may be a single unit, separate from both the breath processing and data processing units. Or the mouthpiece and receiver may be combined with the breath processing unit, in turn then connected to a data processing unit. If miniaturization is a primary goal, all of the compounds may be combined into a single unit with appropriate physical boundaries one from the other. The breath processing unit 20 allows for the flow of exhaled breath over individual sensors, one to monitor for NO and the other for isoprene.

Figure 3:
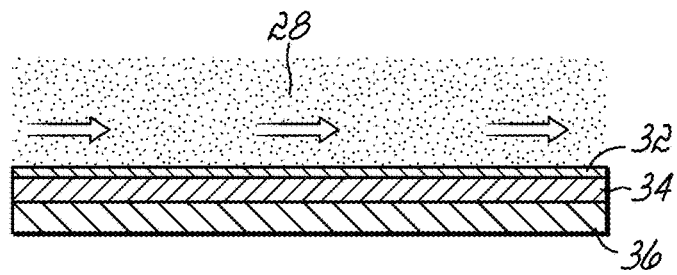
FIG. 3 is a schematic cross-sectional view in further detail of the breath processing unit in FIG. 2.

FIG. 3 is a depiction of a portion of the breath processing unit 20 showing a single metal oxide layer. The unit 20 can include at least one sensor fabricated from a distinct metal oxide to monitor a different biomarker. The exhaled breath particles 28 including NO and isoprene molecules come into contact with the oxide thin-film layer 32. This layer in turn is coupled to the electrode 34, which in turn is coupled to the substrate 36.

In the case of sensing for nitric oxide, the oxide thin-film layer 32 is comprised of γ-$WO_3$ particles arrayed in a thin-film which interact with the NO molecules in the exhaled breath particles 28. In the case of evaluating for isoprene, the oxide thin-film layer 32 is comprised of h-$WO_3$ particles arrayed in a thin-film which interact with isoprene molecules in the exhaled breath particles component 28. Where both NO and isoprene are being sensed, distinct thin film layers of γ-$WO_3$ and h-$WO_3$ are separately applied to discrete electrodes 34, with discrete conductance or resistance change data being transmitted to the data processing unit 24. Information stored in the data processing unit 24 can be subsequently transmitted via wire or wirelessly (such as Bluetooth) to a downstream data storage or processing device.

With the binary sensor array, the goal is to detect not only individual compounds from the subject's exhaled breath, in this instance nitric oxide and isoprene, but to do so quickly and accurately. This binary sensor array utilizes two distinct semi-conducting metal oxides (SMOs) which are fabricated by selecting certain tungsten oxides (γ-$WO_3$ and h-$WO_3$), using the Tethis NP 10 unit to pyrolyze the oxides onto a platinum or gold electrode, which in turn is coupled to an alumina substrate as shown in the Figures above. The electrode is powered with a current, the entire unit is heated so that the molecules to be sensed are in a steady-state, and when target molecules contact the particular tungsten oxide surface having the requisite sensitivity, those molecules cause a change in the resistance or conductance of the particular oxide layer which is sensed through the electrode. This change in resistance or conductance is conveyed to the data processing unit 24 as an electrical change which is a function of the concentration of that molecule in the exhaled breath. The γ-$WO_3$ oxide layer is selective to nitric oxide, and the h-$WO_3$ sensor has the highest selectivity for isoprene in an operational temperature, that temperature depending on the particle size of the oxides comprising the film. Typically, the operational temperature will be between 200 and 350° C.

To quantify the concentration of the particular biomarker via operation of the individual NO and isoprene sensors, the sensors calibrate using pure nitric oxide or isoprene to determine a resistance or conductance change specific to the sensor in light of a known concentration of biomarker compound.

Once the sensor is placed online, response time to determine a concentration of the biomarker material takes approximately 15 seconds. The recovery time between individual sensing runs varies between approximately 90 to 120 seconds.

For a specific sensor operating at a specified temperature, the variation of the sensor resistance or conductance is at most two orders of magnitude. However, as the designated readout circuit is intended to be used with different sensors that can operate at different temperatures, it is assumed that the resistance of the individual sensors can vary over a wide range, from 2 kΩ) to 100 MΩ) (ohms).

While the invention has been illustrated by a description of various embodiments, and while these embodiments have been described in considerable detail, it is not the intention of the Applicant to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the spirit or scope of the Applicant's general inventive concept.

What is claimed is:

1. A method for measuring levels of nitric oxide and isoprene in exhaled breath from a subject comprising:
    exhaling breath into a receiver;
    transferring the breath into a breath processing unit connected to the receiver and heated within a range of 25 to 400° C.;
    contacting the breath with a surface of $\gamma$-$WO_3$ inside the breath processing unit which responds to nitric oxide, and a surface of h-$WO_3$ inside the breath processing unit which responds to isoprene to alter an electrical property of the $\gamma$-$WO_3$ surface and the h-$WO_3$ surface, wherein the $\gamma$-$WO_3$ surface is undoped and the h-$WO_3$ surface is undoped; and
    correlating the electrical property of the $\gamma$-$WO_3$ surface with a concentration of nitric oxide in the breath, and the electrical property of the h-$WO_3$ surface with a concentration of isoprene in the breath.

2. The method of claim 1 wherein the receiver and the breath processing unit are integrated into a single combined unit.

3. The method of claim 1 wherein the surface of the $\gamma$-$WO_3$ and the surface of h-$WO_3$ are separately coupled to electrodes of platinum or gold.

4. The method of claim 3 wherein the electrodes are coupled to an alumina substrate.

5. The method of claim 1 wherein the breath processing unit is heated within a range of 150 to 400° C.

6. The method of claim 1 wherein the breath processing unit is heated within a range of 200 to 350° C.

7. The method of claim 1 wherein the breath processing unit is heated within a range of 250 to 350° C.

8. The method of claim 1 wherein the levels of nitric oxide and isoprene are monitored continuously.

9. The method of claim 1 wherein the subject is a fighter pilot operating an aircraft.

10. The method of claim 1 to evaluate for high altitude pulmonary edema.

11. The method of claim 1 to evaluate for asthma.

12. The method of claim 1 to evaluate for an hypoxic episode.

13. The method of claim 1 to evaluate for insomnia.

* * * * *